United States Patent
Vetter et al.

(10) Patent No.: US 12,378,219 B2
(45) Date of Patent: Aug. 5, 2025

(54) CRYSTALLINE FORMS OF A MAGL INHIBITOR

(71) Applicant: H. LUNDBECK A/S, Valby (DK)

(72) Inventors: Thomas Vetter, Valby (DK); John J. M. Wiener, San Diego, CA (US); Cheryl A. Grice, Redwood City, CA (US); Daniel J. Buzard, San Diego, CA (US); Justin S. Cisar, San Diego, CA (US); Olivia Delene Weber, San Diego, CA (US); Amy Allan, San Diego, CA (US); Nicholas Raffaele, SanDiego, CA (US); Jeanne V. Moody, San Diego, CA (US); Michael B. Shaghafi, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 68 days.

(21) Appl. No.: 18/311,759

(22) Filed: May 3, 2023

(65) Prior Publication Data

US 2023/0357190 A1    Nov. 9, 2023

Related U.S. Application Data

(60) Provisional application No. 63/338,252, filed on May 4, 2022.

(51) Int. Cl.
| | | |
|---|---|---|
| C07D 401/12 | (2006.01) | |
| A61K 31/501 | (2006.01) | |
| A61P 25/00 | (2006.01) | |

(52) U.S. Cl.
CPC .......... *C07D 401/12* (2013.01); *A61K 31/501* (2013.01); *A61P 25/00* (2018.01); *C07B 2200/13* (2013.01)

(58) Field of Classification Search
CPC .... C07D 401/12; C07B 2200/13; A61P 25/00
See application file for complete search history.

(56) References Cited

U.S. PATENT DOCUMENTS

| | | | |
|---|---|---|---|
| 9,133,148 | B2 | 9/2015 | Cisar et al. |
| 10,030,020 | B2 | 7/2018 | Cisar et al. |
| 10,781,211 | B2 | 9/2020 | Cisar et al. |
| 11,059,822 | B2 | 7/2021 | Grice et al. |
| 11,434,222 | B2 | 9/2022 | Wiener et al. |
| 11,691,975 | B2 | 7/2023 | Grice et al. |
| 2011/0172230 | A1 | 7/2011 | Ishii et al. |
| 2016/0137649 | A1 | 5/2016 | Jones et al. |

(Continued)

FOREIGN PATENT DOCUMENTS

| | | |
|---|---|---|
| CN | 110267962 A | 9/2019 |
| JP | 2009514935 A | 4/2009 |

(Continued)

OTHER PUBLICATIONS

Muller-Vahl et al., Pharmacopsychiatry, 55, 148-56 (Year: 2022).*

(Continued)

*Primary Examiner* — Adam C Milligan
*Assistant Examiner* — Jason Nolan
(74) *Attorney, Agent, or Firm* — WILSON SONSINI GOODRICH & ROSATI

(57) ABSTRACT

Described herein are crystalline forms of the MAGL inhibitor 1,1,1,3,3,3-Hexafluoropropan-2-yl(S)-1-(pyridazin-3-yl-carbamoyl)-6-azaspiro[2.5]octane-6-carboxylate.

9 Claims, 8 Drawing Sheets

(56) References Cited

U.S. PATENT DOCUMENTS

| | | | |
|---|---|---|---|
| 2021/0230145 A1 | 7/2021 | Blankman et al. | |
| 2024/0018120 A1 | 1/2024 | Wiener et al. | |

FOREIGN PATENT DOCUMENTS

| | | |
|---|---|---|
| JP | 2014005245 A | 1/2014 |
| WO | WO-2010089510 A2 | 8/2010 |
| WO | WO-2010141817 A1 | 12/2010 |
| WO | WO-2011151808 A1 | 12/2011 |
| WO | WO-2013103973 A1 | 7/2013 |
| WO | WO-2014048865 A1 | 4/2014 |
| WO | WO-2015003002 A1 | 1/2015 |
| WO | WO-2015154023 A1 | 10/2015 |
| WO | WO-2016149401 A2 | 9/2016 |
| WO | WO-2017021805 A1 | 2/2017 |
| WO | WO-2017171100 A1 | 10/2017 |
| WO | WO-2017197192 A1 | 11/2017 |
| WO | WO-2018093946 A1 | 5/2018 |
| WO | WO-2018093947 A1 | 5/2018 |
| WO | WO-2018093949 A1 | 5/2018 |
| WO | WO-2018093950 A1 | 5/2018 |
| WO | WO-2018093953 A1 | 5/2018 |
| WO | WO-2018134698 A1 | 7/2018 |
| WO | WO-2019046318 A1 | 3/2019 |
| WO | WO-2019046330 A1 | 3/2019 |
| WO | WO-2022101412 A1 | 5/2022 |
| WO | WO-2022104079 A1 | 5/2022 |

OTHER PUBLICATIONS

Clinical Trial ID NCT05046119; accessed Nov. 26, 2024 from https://clinicaltrials.gov/search?term=MAGL (Year: 2021).*
Clinical Trial ID NCT04324710; accessed Nov. 26, 2024 from https://clinicaltrials.gov/search?term=MAGL (Year: 2020).*
Clinical Trial ID NCT03100136; accessed Nov. 26, 2024 from https://clinicaltrials.gov/search?term=MAGL (Year: 2017).*
Clinical Trial ID NCT05219838; accessed Nov. 26, 2024 from https://clinicaltrials.gov/search?term=MAGL (Year: 2022).*
Clinical Trial ID NCT04419636; accessed Nov. 26, 2024 from https://clinicaltrials.gov/search?term=MAGL (Year: 2021).*
Conner, S., Glaxo chief: Our drugs do not work on most patients, The Independent (Year: 2003).*
Granchi et al., Chapter 20 in Rational Drug Design: Methods and Protocols, Methods in Molecular Biology, Mavromoustakos and Kellici (eds), 335-46, 336 (Year: 2018).*
Bedse et al. Therapeutic endocannabinoid augmentation for mood and anxiety disorders: comparative profiling of FAAH. Translational Psychiatry 8:92 (2018).
Ben-Ari et al. Electrographic, clinical and pathological alterations following systemic administration of kainic acid, bicuculline or pentetrazole: metabolic mapping using the deoxyglucose method with special reference to the pathology of epilepsy. Neuroscience 6:1361-1391 (1981).
Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Collin et al. A double-blind, randomized, placebo-controlled, parallel-group study of Sativex, in subjects with symptoms of spasticity due to multiple sclerosis. Neurol Res 32(5):451-459 (2010).
Collin et al. Randomized controlled trial of cannabis-based medicine in spasticity caused by multiple sclerosis. Eur J Neurol 14(3):290-296 (2007).
Fiz et al. Cannabis use in patients with fibromyalgia: effect on symptoms relief and health-related quality of life. PLoS One 6(4):e18440 (2011).
Fleisher et al. Improved oral drug delivery: solubility limitations overcome by the use of prodrugs. Advanced Drug Delivery Reviews 19:115-130 (1996).
Gil-Ordonez et al. Monoacylglycerol lipase (MAGL) as a promising therapeutic target. Biochem Pharmacol 157:18-32 (2018).
Grabner et al. Monoglyceride lipase as a drug target: At the crossroads of arachidonic acid metabolism and endocannabinoid signaling. Pharmacol Ther 175:35-46 (2017).
He et al. Determination of absolute configuration of chiral molecules using vibrational optical activity: a review. Appl. Spectrosc. 65(7):699-723 (2011).
Hill et al. Integrating Endocannabinoid Signaling and Cannabinoids into the Biology and Treatment of Posttraumatic Stress Disorder. Neuropsychopharmacology 43(1):80-102 (2018).
Hill. Medical Marijuana for Treatment of Chronic Pain and Other Medical and Psychiatric Problems: A Clinical Review. JAMA 313(24):2474-2483 (2015).
Ilyasov et al. The endocannabinoid system and oligodendrocytes in health and disease. Front Neurosci 12:733 (2018).
Kano et al. Endocannabinoid-mediated control of synaptic transmission. Physiol Rev 8:309-380 (2009).
Katona et al. Endocannabinoid signalling as a synaptic circuit breaker in neurological disease. Nat Med. 14(9):923-93 (2008).
Keith et al. Heteroarylureas with spirocyclic diamine cores as inhibitors of fatty acid amide hydrolase. Bioorg Med Chem Lett 24(3):737-41 (2014).
Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).
Long et al. Characterization of tunable piperidine and piperazine carbamates as inhibitors of endocannabinoid hydrolases. J Med chem 53(4):1830-1842 (2010).
Long et al. Selective blockade of 2-arachidonoylglycerol hydrolysis produces cannabinoid behavioral effects. Nat Chem Biol. 5(1):37-44 (2009).
Mease et al. A randomized, double-blind, placebo-controlled, phase III trial of pregabalin in the treatment of patients with fibromyalgia. J Rheumatol 35(3):502-514 (2008).
Mulvihill et al. Therapeutic potential of monoacylglycerol lipase inhibitors. Life Sci 92(8-9):492-497 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Endocannabinoid hydrolysis generates brain prostaglandins that promote neuroinflammation. Science 334(6057):809-813 (2011).
PCT/EP2021/081522 International Search Report and Written Opinion dated Feb. 7, 2022.
Pryce et al. Endocannabinoids in Multiple Sclerosis and Amyotrophic Lateral Sclerosis. Handb Exp Pharmacol 231:213-31 (2015).
Pubchem, Substance Database, SID 239803465. Retrieved from Internet: <URL: https://pubchem.ncbi.nlm.nih.gov/substance/239803465> ( 7pgs.) (Available Date Feb. 13, 2015) (retrieved Jun. 27, 2017).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Skrabek et al. Nabilone for the treatment of pain in fibromyalgia. J Pain 9(2):164-173 (2008).
Sugaya et al. Crucial Roles of the Endocannabinoid 2-Arachidonoylglycerol in the Suppression of Epileptic Seizures. Cell Rep 16(5):1405-1415 (2016).
Turcotte et al. Nabilone as an adjunctive to gabapentin for multiple sclerosis-induced neuropathic pain: a randomized controlled trial. Pain Med 16(1):149-159 (2015).
Turcotte et al. The CB2 receptor and its role as a regulator of inflammation. Cell. Mol. Life Sci. 73:4449-4470 (2016).
U.S. Appl. No. 17/524,632 Office Action dated Jan. 7, 2022.
Ware et al. The effects of nabilone on sleep in fibromyalgia: results of a randomized controlled trial. Anesth Analg 110(2):604-610 (2010).

(56) References Cited

OTHER PUBLICATIONS

Whiting et al. Cannabinoids for Medical Use: A Systematic Review and Meta-analysis. JAMA 313(24):2456-2473 (2015).
Zajicek et al. Cannabinoids for treatment of spasticity and other symptoms related to multiple sclerosis (CAMS study): multicentre randomised placebo-controlled trial. Lancet 362(9395):1517-1526 (2003).
Burckhardt et al. The fibromyalgia impact questionnaire: development and validation. J Rheumatol 18(5):728-733 (1991).
PCT/EP2023/061626 International Search Report and Written Opinion dated Jul. 6, 2023.

* cited by examiner

CRYSTALLINE FORMS OF A MAGL INHIBITOR

CROSS-REFERENCE

This application claims benefit of provisional U.S. Application No. 63/338,252, filed May 4, 2022, which is herein incorporated by reference in its entirety.

FIELD OF THE INVENTION

The present invention relates to crystalline forms of 1,1,1,3,3,3-Hexafluoropropan-2-yl (S)-1-(pyridazin-3-ylcarbamoyl)-6-azaspiro[2.5]octane-6-carboxylate, pharmaceutical compositions comprising such crystalline forms and methods and uses for treating various disorders that would benefit from inhibition of monoacylglycerol lipase (MAGL).

BACKGROUND OF THE INVENTION

MAGL is a member of the serine hydrolase superfamily. MAGL is expressed throughout the brain, in neurons, microglia, astrocytes, and oligodendrocytes. MAGL is the primary enzyme controlling the degradation of 2-arachidonoylglycerol (2-AG) to arachidonic acid (AA) (Blankman et al. Chem Biol. 2007; Nomura et al. Science. 2011).

2-AG is the most abundant endocannabinoid ligand in the brain where it acts as a retrograde messenger to reduce excessive neurotransmission via the activation of pre-synaptic $CB_1$ receptors (Katona et al., Nat Med. 2008 September; 14(9):923-30), regulating immune response via the activation of microglial $CB_2$ receptors (Turcotte et al. Cell Mol Life Sci. 2016 December; 73(23):4449-4470), and promote neuroprotection via e.g., its effects on oligodendrocyte production and survival (Front Neurosci. 2018 Oct. 26; 12:733).

AA is one of the most abundant fatty acids in the brain and the main precursor of eicosanoids such as prostanoids and leukotrienes that are known inflammatory mediators.

MAGL is at the crossroads between the endocannabinoid and eicosanoid signaling systems. Inhibiting the action or activation of MAGL is a promising therapeutic approach for the prevention or treatment of brain disorders whose pathological hallmarks include excessive neurotransmission, neuroinflammation or neurodegeneration such as Alzheimer's disease (AD), Parkinson's disease (PD), Huntington's disease (HD), multiple sclerosis (MS), amyotrophic lateral sclerosis (ALS), traumatic brain injury, stroke, epilepsy, pain, migraine, addiction, anxiety, depression and other stress-related disorders (Grabner et al. Pharmacol Ther. 2017 July; 175:35-46; Mulvihill et al. Life Sci. 2013 Mar. 19; 92(8-9):492-7; Gil-Ordóñez et al. Biochem Pharmacol. 2018 November; 157:18-32).

The development of solid forms is highly complex, because it is not possible to predict from previous experience if various solid forms of a compound exist, let alone how to make them.

Even after a solid form has been synthesized, the identification and selection of a solid form for further pharmaceutical development are complex, given that a change in a solid form may affect a variety of physical and chemical abilities which are unpredictable and may provide benefits or drawbacks in areas of pharmaceutical development such as processing, formulation, stability, bioavailability, or storage.

From this background it is still not possible to predict whether a particular compound will form polymorphs, whether any such polymorphs will be suitable for commercial use in a therapeutic composition or which polymorphs will display such desirable properties. Hence, there is still an unmet need for making solid forms for further pharmaceutical development with desirable properties such as stability.

SUMMARY OF THE INVENTION

An object of the invention is to provide a solid form of 1,1,1,3,3,3-Hexafluoropropan-2-yl (S)-1-(pyridazin-3-ylcarbamoyl)-6-azaspiro[2.5]octane-6-carboxylate suitable for pharmaceutical development.

Accordingly in a first aspect of the invention is provided a crystalline form of 1,1,1,3,3,3-Hexafluoropropan-2-yl (S)-1-(pyridazin-3-ylcarbamoyl)-6-azaspiro[2.5]octane-6-carboxylate.

In another aspect of the invention is provided a solid dosage form comprising a crystalline form of 1,1,1,3,3,3-Hexafluoropropan-2-yl(S)-1-(pyridazin-3-ylcarbamoyl)-6-azaspiro[2.5]octane-6-carboxylate, and one or more pharmaceutically acceptable carriers or diluents.

In a further aspect of the invention is provided a crystalline form of 1,1,1,3,3,3-Hexafluoropropan-2-yl (S)-1-(pyridazin-3-ylcarbamoyl)-6-azaspiro[2.5]octane-6-carboxylate for use in the treatment of diseases or disorders benefiting from inhibiting activation of MAGL.

INCORPORATION BY REFERENCE

All publications and patent applications mentioned in this specification are herein incorporated by reference to the extent applicable and relevant.

DETAILED DESCRIPTION OF THE INVENTION

Definitions

Figure 1:
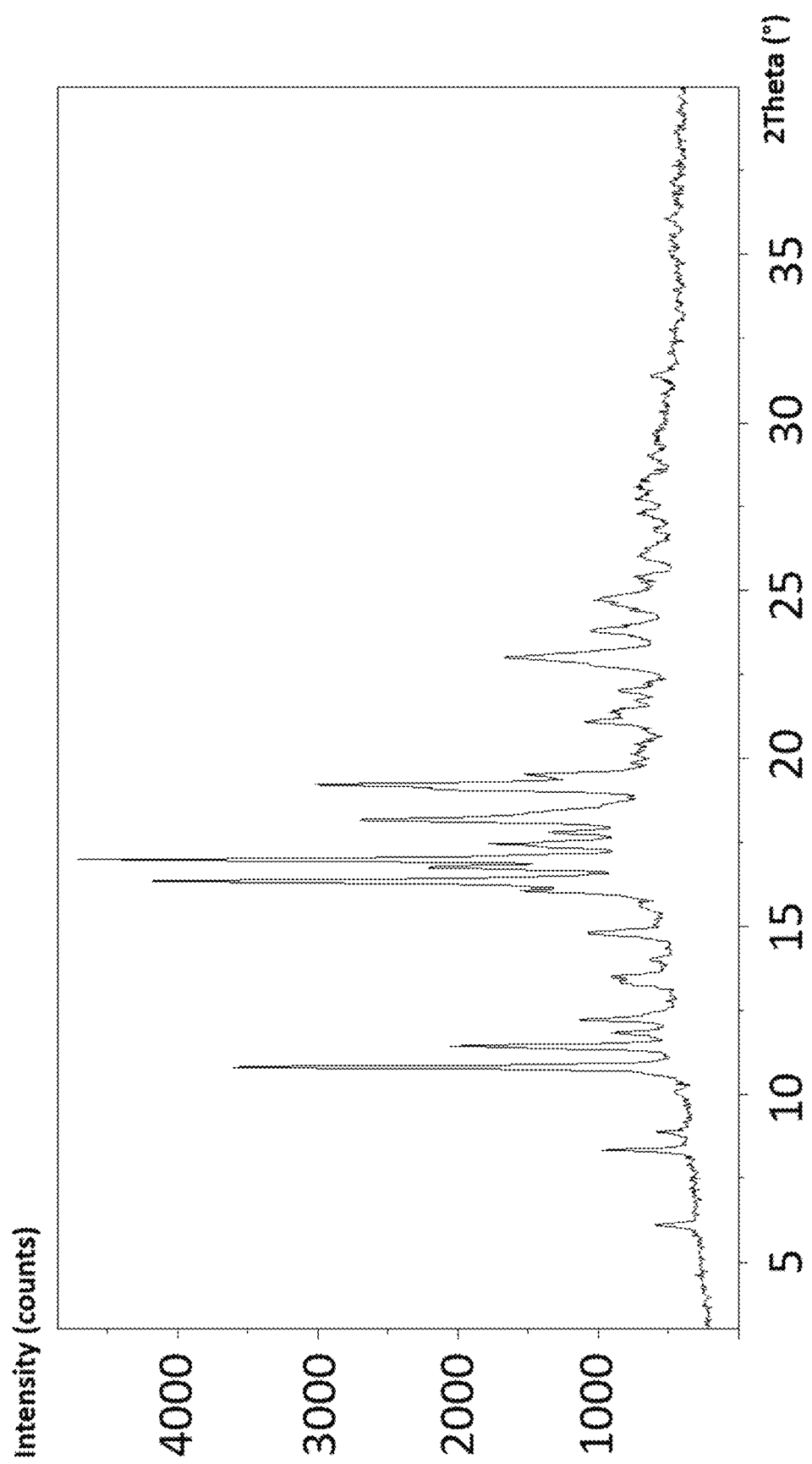
FIG. 1 shows an X-ray powder diffraction (XRPD) pattern of Compound (I) form 1. X-axis: diffraction angle (°2θ); Y-axis: intensity (counts).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound (I), age, weight, general condition of the subject, the condition being treated, the severity of the condition being treated, and the judgment of the prescribing physician.

The terms "inhibits", "inhibiting", or "inhibitor" of an enzyme as used herein, refer to inhibition of enzymatic activity.

The term "subject" as used herein, refers to an animal which is the object of treatment, observation or experiment. By way of example only, a subject may be, but is not limited to, a mammal including, but not limited to, a human. In an embodiment, the subject is a human.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

The X-ray diffraction data provided herein is indicated to a precision of ±0.1°2θ.

Compounds

The compound, 1,1,1,3,3,3-Hexafluoropropan-2-yl (S)-1-(pyridazin-3-ylcarbamoyl)-6-azaspiro[2.5]octane-6-carboxylate, designated herein as Compound (I), has the structure:

Compound (I)

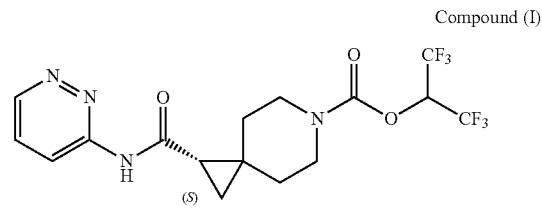

The present invention relates to crystalline forms of Compound (I), and the use of the compounds for treating various disease and disorder which is believed to be linked to the regulation of endocannabinoid system signaling activities. The present invention further provides crystalline forms of Compound (I) described herein as "Compound (I) form 1" and "Compound (I) form 3". These are free forms of Compound (I). The term "free form" refers to Compound (I) in non-salt form.

While not intending to be bound by any particular theory, certain crystalline forms have different physical and chemical properties, e.g., stability, solubility and dissolution rate, appropriate for pharmaceutical and therapeutic dosage forms. Moreover, while not wishing to be bound by any particular theory, certain solid forms have different physical and chemical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Embodiments of the Invention

In the following, embodiments of the invention are disclosed. The first embodiment is denoted E1, the second embodiment is denoted E2 and so forth.

E1. A crystalline form of 1,1,1,3,3,3-Hexafluoropropan-2-yl (S)-1-(pyridazin-3-ylcarbamoyl)-6-azaspiro[2.5]octane-6-carboxylate.

Figure 2:
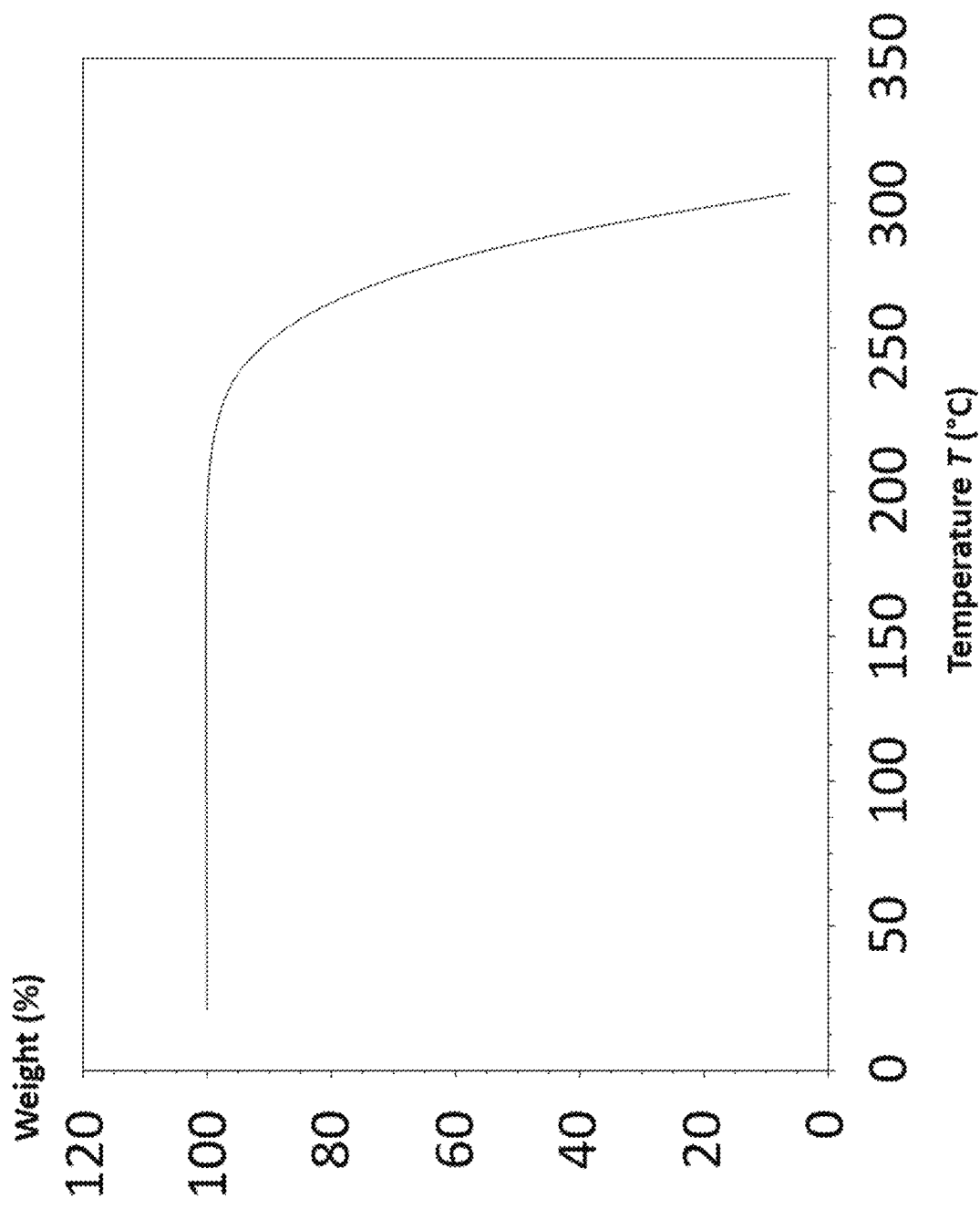
FIG. 2 shows a thermo-gravimetric analysis (TGA) thermogram of Compound (I) form 1. X-axis: Temperature (° C.); Y-axis: Weight (%).

E2. The crystalline form according to embodiment E1, wherein the crystalline form is 1,1,1,3,3,3-Hexafluoropropan-2-yl (S)-1-(pyridazin-3-ylcarbamoyl)-6-azaspiro[2.5]octane-6-carboxylate form 1 having at least one of the following properties:
   a) an X-ray powder diffraction (XRPD) obtained using CuK$_{\alpha1}$ radiation (λ=1.5406 Å) showing an XRPD pattern substantially the same as shown in FIG. 1;
   b) an X-ray powder diffraction (XRPD) pattern obtained using CuK$_{\alpha1}$ radiation (λ=1.5406 Å) showing characteristic peaks at the following 2Θ-angles: 10.81°, 16.54°, 16.76°, and 19.21°;
   c) a thermo-gravimetric analysis (TGA) substantially similar to the one set forth in FIG. 2;
   d) combination thereof.

E3. The crystalline form according to embodiment E2, wherein the crystalline form is 1,1,1,3,3,3-Hexafluoropropan-2-yl (S)-1-(pyridazin-3-ylcarbamoyl)-6-azaspiro[2.5]octane-6-carboxylate form 1 having a crystal form characterized by an XRPD obtained using CuK$_{\alpha1}$ radiation (λ=1.5406 Å) showing peaks at the following 2Θ-angles: 10.81°, 16.54°, 16.76°, and 19.21°.

Figure 3:
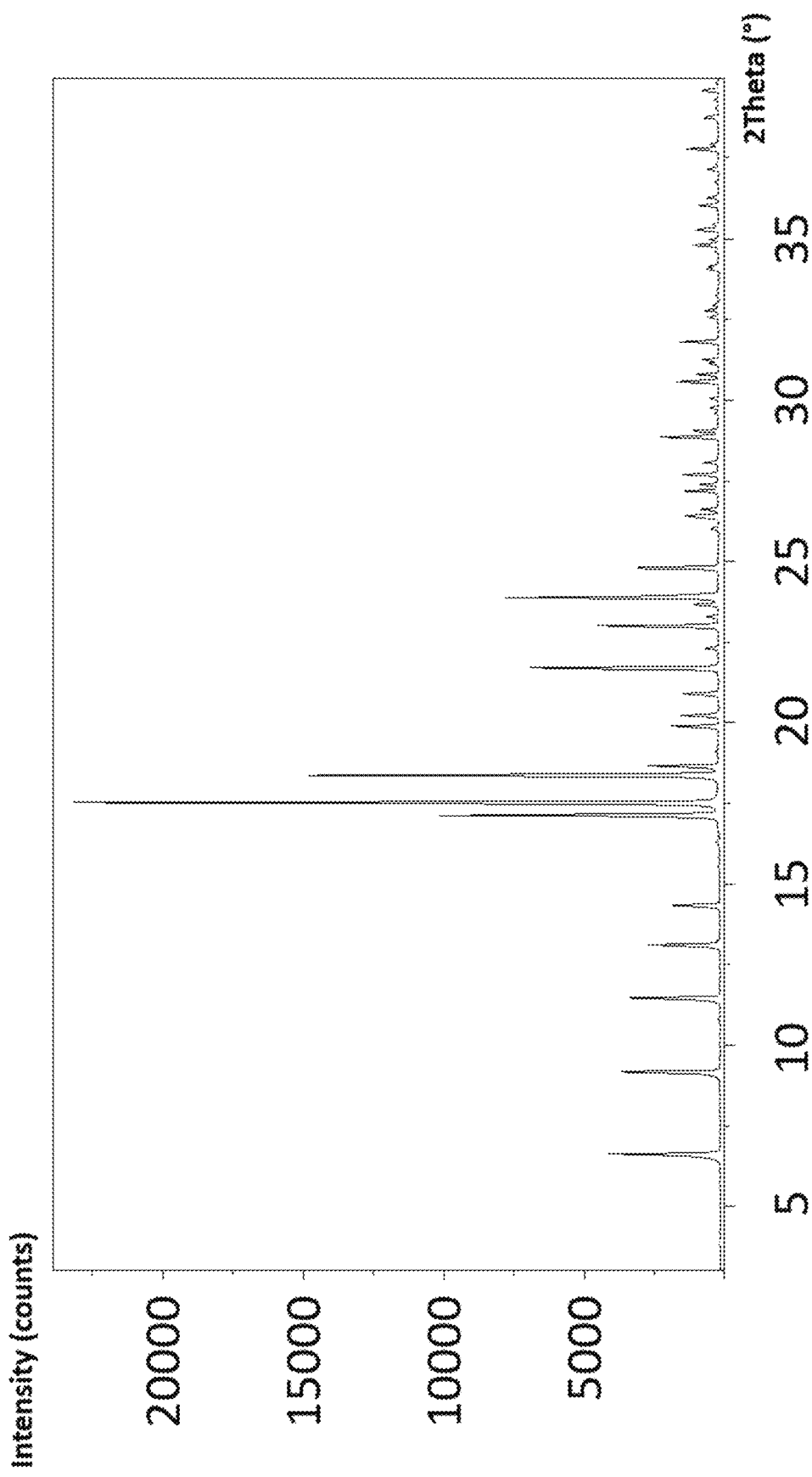
FIG. 3 shows an X-ray powder diffraction (XRPD) pattern of Compound (I) form 3. X-axis: diffraction angle (°2θ); Y-axis: intensity (counts).
Figure 4:
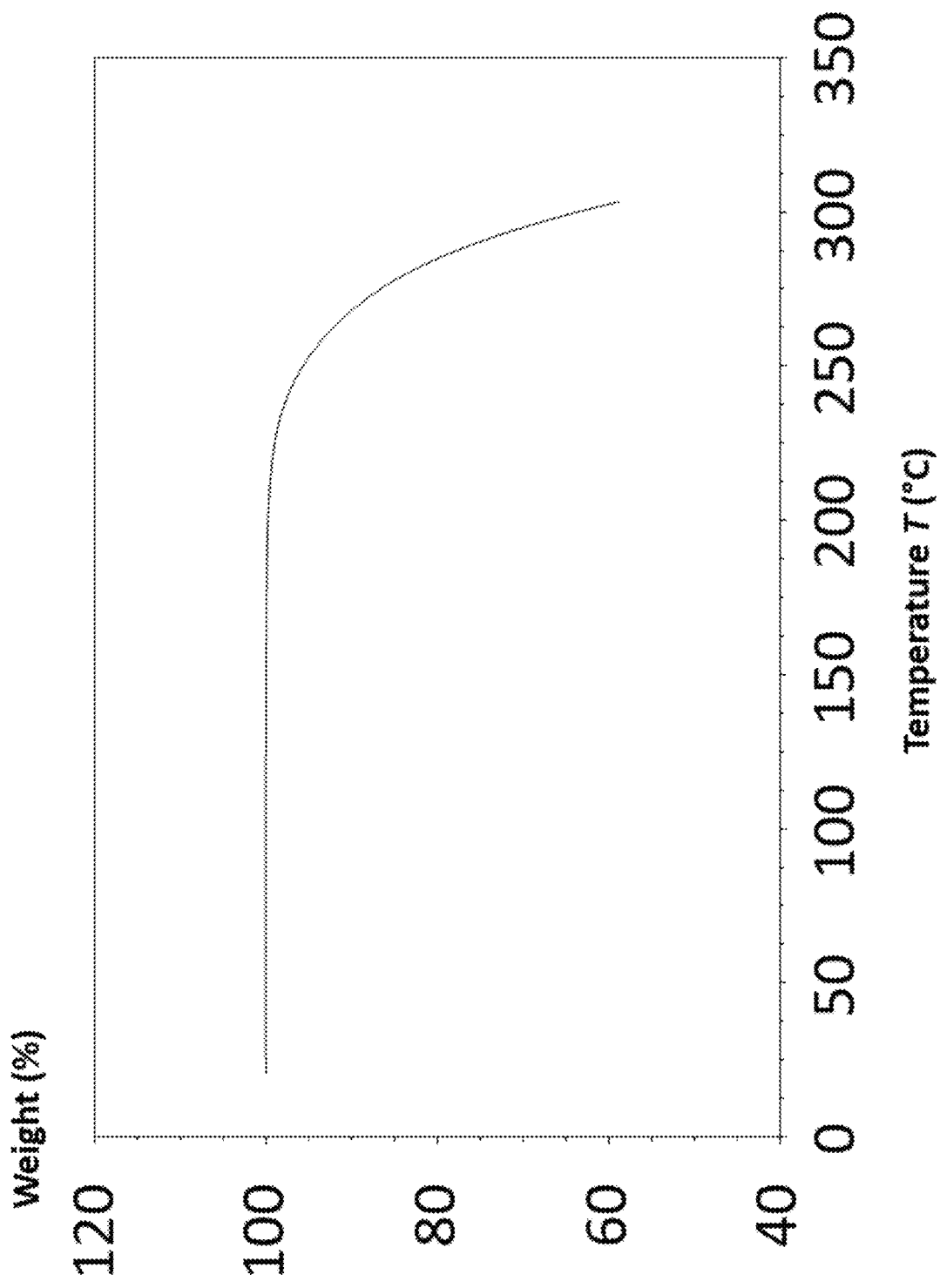
FIG. 4 shows a thermo-gravimetric analysis (TGA) thermogram of Compound (I) form 3. X-axis: Temperature (° C.); Y-axis: Weight (%).

E4. The crystalline form according to embodiment E1, wherein the crystalline form is 1,1,1,3,3,3-Hexafluoropropan-2-yl (S)-1-(pyridazin-3-ylcarbamoyl)-6-azaspiro[2.5]octane-6-carboxylate form 3 having at least one of the following properties:
   a) an X-ray powder diffraction (XRPD) obtained using CuK$_{\alpha1}$ radiation (λ=1.5406 Å) showing an XRPD pattern substantially the same as shown in FIG. 3;
   b) an X-ray powder diffraction (XRPD) pattern obtained using CuK$_{\alpha1}$ radiation (λ=1.5406 Å) showing characteristic peaks at the following 2Θ-angles: 6.61°, 9.16°, 13.09°, and 14.32°;
   c) a thermo-gravimetric analysis (TGA) substantially similar to the one set forth in FIG. 4;
   d) combination thereof.

E5. The crystalline form according to embodiment E4, wherein the crystalline form is 1,1,1,3,3,3-Hexafluoropropan-2-yl (S)-1-(pyridazin-3-ylcarbamoyl)-6-azaspiro[2.5]octane-6-carboxylate form 3 having a crystal form characterized by an XRPD obtained using CuK$_\alpha$ radiation (λ$_1$=1.5406 Å, λ$_2$=1.5444 Å) showing peaks at the following 2Θ-angles: 6.61°, 9.16°, 13.09°, and 14.32°.

E6. A solid dosage form comprising a crystalline form according to any one of embodiments E1-E5, and one or more pharmaceutically acceptable carriers or diluents.

E7. The solid dosage form according to embodiment E6, wherein the solid dosage form is selected from capsules, tablets, dragées, pills, lozenges, powders and granules.

E8. The solid dosage form according to embodiment E7, wherein the solid dosage form is a tablet.

E9. The solid dosage form according to embodiment E7, wherein the solid dosage form is a capsule.

E10 The dosage form according to any one of embodiments E7-E9, wherein the dosage form containing a crystalline form of 1,1,1,3,3,3-Hexafluoropropan-2-yl (S)-1-(pyridazin-3-ylcarbamoyl)-6-azaspiro[2.5]octane-6-carboxylate according to embodiments E1-E5 in an amount of about 0.1 to 500 mg.

E11. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 0.1 to 200 mg.

E12. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 2 to 200 mg.

E13. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 2 to 100 mg.

E14. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 2 to 50 mg.

E15. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 5 to 50 mg.

E16. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 10 to 50 mg.

E17. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 10 to 100 mg.

E18. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 1 to 50 mg.

E19. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 1 to 40 mg.

E20. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 1 to 20 mg.

E21. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 1 to 10 mg.

E22. The dosage form according to embodiment E10, wherein the dosage form contains the crystalline form of 1,1,1,3,3,3-Hexafluoropropan-2-yl (S)-1-(pyridazin-3-ylcarbamoyl)-6-azaspiro[2.5]octane-6-carboxylate in an amount from of about 10 to 20 mg E23. The dosage form according to any one of embodiments E6-E22, wherein the crystalline form is selected from 1,1,1,3,3,3-Hexafluoropropan-2-yl (S)-1-(pyridazin-3-ylcarbamoyl)-6-azaspiro[2.5]octane-6-carboxylate form 1 or 1,1,1,3,3,3-Hexafluoropropan-2-yl (S)-1-(pyridazin-3-ylcarbamoyl)-6-azaspiro[2.5]octane-6-carboxylate form 3.

E24. The dosage form according to any one of embodiments E6-E22, wherein the crystalline form is 1,1,1,3,3,3-Hexafluoropropan-2-yl (S)-1-(pyridazin-3-ylcarbamoyl)-6-azaspiro[2.5]octane-6-carboxylate form 1.

E25. The dosage form according to any one of embodiments E6-E22, wherein the crystalline form is 1,1,1,3,3,3-Hexafluoropropan-2-yl (S)-1-(pyridazin-3-ylcarbamoyl)-6-azaspiro[2.5]octane-6-carboxylate form 3.

E26. A tablet containing about 0.1-200 mg of the crystalline form according to any one of embodiments E1-E5, and one or more pharmaceutically acceptable carriers or diluents.

E27. The tablet according to embodiment E26, wherein the tablet containing about 2-100 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E28. The tablet according to embodiment E26, wherein the tablet containing about 10-100 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E29. The tablet according to embodiment E26, wherein the tablet containing about 1-20 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E30. The tablet according to embodiment E26, wherein the tablet containing about 1-40 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E31. The tablet according to embodiment E26, wherein the tablet containing about 5-30 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E32. The tablet according to embodiment E26, wherein the tablet containing about 10-20 mg of the crystalline form of 1,1,1,3,3,3-Hexafluoropropan-2-yl (S)-1-(pyridazin-3-ylcarbamoyl)-6-azaspiro[2.5]octane-6-carboxylate of any one of embodiments E1-E5.

E33. The crystalline form of 1,1,1,3,3,3-Hexafluoropropan-2-yl (S)-1-(pyridazin-3-ylcarbamoyl)-6-azaspiro[2.5]octane-6-carboxylate according to any one of embodiments E1 to E5 or the dosage form according to any one of embodiments E6-E32, for use in the treatment of a disease or disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, post-traumatic stress disorder, renal ischemia, rheumatoid arthritis, skeletal muscle contusion, skin diseases, spacsticity, spacsticity in patient with multiple sclerosis, sunburn, systemic lupus erythematosus, toothache, epilepsy, treatment resistant focal epilepsy, vasoocclusive painful crises in sickle cell disease, and visceral pain.

E34. The crystalline form of 1,1,1,3,3,3-Hexafluoropropan-2-yl (S)-1-(pyridazin-3-ylcarbamoyl)-6-azaspiro[2.5]octane-6-carboxylate for use according to embodiment E33, wherein the disease or disorder is spacsticity.

E35. The crystalline form of 1,1,1,3,3,3-Hexafluoropropan-2-yl (S)-1-(pyridazin-3-ylcarbamoyl)-6-azaspiro[2.5]octane-6-carboxylate for use according to embodiment E33, wherein the disease or disorder is multiple sclerosis.

E36. The crystalline form of 1,1,1,3,3,3-Hexafluoropropan-2-yl (S)-1-(pyridazin-3-ylcarbamoyl)-6-azaspiro[2.5]octane-6-carboxylate for use according to embodiment E33, wherein the disease or disorder is spacsticity in patient with multiple sclerosis.

E37. The crystalline form of 1,1,1,3,3,3-Hexafluoropropan-2-yl (S)-1-(pyridazin-3-ylcarbamoyl)-6-azaspiro[2.5]octane-6-carboxylate for use according to embodiment E33, wherein the disease or disorder is epilepsy.

E38. The crystalline form of 1,1,1,3,3,3-Hexafluoropropan-2-yl (S)-1-(pyridazin-3-ylcarbamoyl)-6-azaspiro[2.5]octane-6-carboxylate for use according to embodiment E33, wherein the disease or disorder is treatment resistant focal epilepsy.

E39. A method for the treatment of disease or a disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, post-traumatic stress disorder, renal ischemia, rheumatoid arthritis, skeletal muscle contusion, skin diseases, sunburn, systemic lupus erythematosus, toothache, epilepsy, treatment resistant focal epilepsy, vasoocclusive painful crises in sickle cell disease, and visceral pain; which method comprises the administration of a therapeutically effective amount of the crystalline form of 1,1,1,3,3,3-Hexafluoropropan-2-yl (S)-1-(pyridazin-3-ylcarbamoyl)-6-azaspiro[2.5]octane-6-carboxylate according to any of embodiments E1 to E5 or the dosage form according to any one of embodiments E6-E32, to a patient in need thereof.

E40. Use of the crystalline form of 1,1,1,3,3,3-Hexafluoropropan-2-yl (S)-1-(pyridazin-3-ylcarbamoyl)-6-azaspiro[2.5]octane-6-carboxylate according to any of embodiments E1 to E5 or the dosage form according to any one of embodiments E6-E32, in the manufacture of a medicament for the treatment of disease or a disorder selected from atopic dermatitis, bladder dysfunction associated with multiple sclerosis, cardiovascular disease, contact dermatitis, cystic fibrosis, dermatomyositis, eczema, endometriosis, enteritis, fibromyalgia, inflammatory bowel disease, interstitial cystitis, irritable bowel syndrome, ischemia, labor, abdominal pain, abdominal pain associated with irritable bowel syndrome, acute pain, back pain, cancer pain, chest pain, functional chest pain, joint pain, menstrual pain, metabolic disorders, musculoskeletal diseases, peripheral neuropathy, migraine, visceral hypersensitivity osteoarthritis, pancreatitis, pharyngitis, post mastectomy pain syndrome, post trigeminal neuralgia, post-operative pain, post-traumatic stress disorder, renal ischemia, rheumatoid arthritis, skeletal muscle contusion, skin diseases, sunburn, systemic lupus erythematosus, toothache, epilepsy, treatment resistant focal epilepsy, vasoocclusive painful crises in sickle cell disease, and visceral pain.

E41. 1,1,1,3,3,3-Hexafluoropropan-2-yl (S)-1-(pyridazin-3-ylcarbamoyl)-6-azaspiro[2.5]octane-6-carboxylate, or a pharmaceutically acceptable salt thereof for use in the treatment of treatment resistant focal epilepsy.

E42. 1,1,1,3,3,3-Hexafluoropropan-2-yl (S)-1-(pyridazin-3-ylcarbamoyl)-6-azaspiro[2.5]octane-6-carboxylate, or a pharmaceutically acceptable salt thereof for use in the treatment of post-traumatic stress disorder.

E43. 1,1,1,3,3,3-Hexafluoropropan-2-yl (S)-1-(pyridazin-3-ylcarbamoyl)-6-azaspiro[2.5]octane-6-carboxylate, or a pharmaceutically acceptable salt thereof for use in the treatment of spasticity.

Pharmaceutical Compositions

Crystalline forms of Compound (I) may be in a composition as the sole active ingredient or in combination with other active ingredients. Additionally, one or more pharmaceutically acceptable carriers or diluents may be in the composition.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders and granules. Where appropriate, they can be prepared with coatings. Oral dosage forms, and in particular tablets, are often preferred by the patients and the medical practitioner due to the ease of administration and the consequent better compliance.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, crystalline forms of Compound (I) are administered in a unit dosage form containing said compounds in an amount of about 0.1 to 500 mg, such as 1 mg, 2 mg, 4 mg, 6 mg, 8 mg, 10 mg, 20 mg, 30 mg, 40 mg, 50 mg 100 mg, 150 mg, 200 mg or 250 mg. In another embodiment the unit dosage form containing said compounds in an amount of about 2 mg to 100 mg, such as 5 mg to 100 mg, 10 mg to 100 mg, 15 mg to 100 mg, 20 mg to 100 mg, 25 mg to 100 mg, 30 mg to 100 mg, 35 mg to 100 mg, 40 mg to 100 mg, 45 mg to 100 mg, or 50 mg to 100 mg. In a further embodiment the unit dosage form containing said compounds in an amount of about 2 mg to 50 mg, such as 5 mg to 50 mg, 10 mg to 50 mg, 15 mg to 50 mg, 20 mg to 50 mg, 25 mg to 50 mg, 30 mg to 50 mg, 35 mg to 50 mg, 40 mg to 50 mg, or 45 mg to 50 mg.

For parenteral administration, solutions of the crystalline forms of Compound (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phosphor lipids, fatty acids, fatty acid amines, polyoxyethylene and water. The pharmaceutical compositions formed by combining crystalline forms of Compound (I) and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be a tablet, capsule, or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tablet machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In an embodiment, crystalline 1,1,1,3,3,3-Hexafluoropropan-2-yl (S)-1-(pyridazin-3-ylcarbamoyl)-6-azaspiro[2.5]octane-6-carboxylate is provided in an oral solution comprising buffer, benzoic acid, hydroxypropyl betadex, acesulfame potassium, denatonium benzoate, and water.

Conditions for Treatment

Also disclosed herein are methods of treating and/or preventing having a disease or disorder which may benefit from inhibition of MAGL. Disclosed methods include administering a pharmaceutically effective amount of a crystalline form of Compound (I).

Atopic Dermatitis

Atopic Dermatitis (AD), also known as eczema, is a common chronic inflammatory skin disorder associated with dysfunction of the body's immune system. AD affects up to 20% of children but can extend to adulthood affecting up to 3% of adults. In AD the skin becomes extremely itchy. Excessive scratching leads to redness, swelling, cracking, "weeping" clear fluid and crusting of the skin. A functional endocannabinoid signaling system is present in the skin and mediates multiple aspects of skin biology. Third-party studies indicate that CB1 and CB2 receptors are upregulated in atopic dermatitis and that the endocannabinoid system exerts a protective effect in models of skin allergy. In addition, it has been demonstrated that MAGL inhibitors can decrease MAGL activity and increase levels of 2-AG in rodent skin.

In some embodiments, MAGL inhibitors described herein have efficacy in treating atopic dermatitis. In some embodiments, disclosed herein is a method of treating atopic dermatitis in a patient in need thereof, comprising administering to the patient a therapeutically effective amount of Compound (I) form 1 or Compound (I) form 3. In some embodiments, disclosed herein is a method of treating atopic dermatitis in a patient in need thereof, comprising administering to the patient a therapeutically effective amount of Compound (I) form 1 or Compound (I) form 3.

Fibromyalgia

Fibromyalgia (FM) is a common, chronic, idiopathic condition characterized by diffuse body pain and the presence of pressure allodynia. Several third-party studies of exocannabinoids in FM have indicated activity. For example, measures of pain (e.g., NRS-11, Pain VAS) and the Fibromyalgia Impact Questionnaire (FIQ), which measures limitations in several activities of daily living impacted by FM, have demonstrated activity of drugs in FM clinical trials. In an 8-week, 40-patient study, compared with placebo an exocannabinoid improved pain measured on a 10 cm VAS, and improved the FIQ domain of anxiety and the FIQ total score.

In some embodiments, MAGL inhibitors described herein have efficacy in treatment of FM. In some embodiments, disclosed herein is a method of treating fibromyalgia in a patient in need thereof, comprising administering to the patient a therapeutically effective amount of Compound (I) form 1 or Compound (I) form 3.

Epilepsy and Seizure Treatment

In a study by Sugaya et al., Cell Rep. 2016, it is suggested 2-AG is crucial for suppressing seizures. Hence, in another embodiment, disclosed herein is a crystalline form of Compound (I) for use in the treatment of a epilepsy/seizure disorder. In a further embodiment, disclosed herein is a crystalline form of Compound (I) for use in the treatment-resistant focal epilepsy.

Furthermore, it has been suggested by Yeh et al., Perspectives on the Role of Endocannabinoids in Autism Spectrum Disorders, OBM Neurobiol. 2017. that targeting the endocannabinoid signaling is a potential way forward for treating symptoms within Autism spectrum disorders.

In a further embodiment, disclosed herein is a crystalline form of Compound (I) for use in the treatment of acute repetitive seizures, temporal lobe epilepsy, Dravet syndrome, Lennox Gastaut syndrome or Angelman syndrome.

Migraine

Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options. Third party data suggests that endocannabinoid pathways may be relevant in migraine. In patients with chronic migraine and probable analgesic-overuse headache, CSF samples showed higher levels of the endocannabinoid palmitoylethanolamide and lower levels of anandamide compared with healthy controls. In addition, patients with a primary diagnosis of migraine headaches found a decrease in the frequency of migraine headaches after initiating marijuana therapy.

In some embodiments, MAGL inhibitors described herein have efficacy in treatment of migraine. In some embodiments, disclosed herein is a method of treating migraine in a patient in need thereof, comprising administering to the patient a therapeutically effective amount of Compound (I) form 1 or Compound (I) form 3.

Acute Pain, Inflammatory Pain, Cancer Pain, and Pain Caused by Peripheral Neuropathy MAGL inhibitors have shown efficacy in several rodent models of pain including models of acute pain, inflammatory pain, cancer pain, and pain caused by chemotherapy-induced peripheral neuropathy.

In some embodiments, MAGL inhibitors described herein have efficacy in treatment of Acute Pain, Inflammatory Pain, Cancer Pain, and Pain Caused by Peripheral Neuropathy. In some embodiments, disclosed herein is a method of treating Acute Pain, Inflammatory Pain, Cancer Pain, and Pain Caused by Peripheral Neuropathy in a patient in need thereof, comprising administering to the patient a therapeutically effective amount of Compound (I) form 1 or Compound (I) form 3.

Functional Dyspepsia

Functional dyspepsia (FD) is one of the most common gastrointestinal disorders encountered in clinical practice. Several pathophysiological mechanisms have been proposed to underlie symptom generation in FD, including visceral hypersensitivity due to central or peripheral sensitization, low-grade inflammatory states, altered secretion of gastrointestinal hormones, genetic predisposition, and abnormal gastric emptying or accommodation. Third party data supports the hypothesis that the function of the endocannabinoid system is altered in FD patients.

In some embodiments, MAGL inhibitors described herein have efficacy in treatment of functional dyspepsia. In some embodiments, disclosed herein is a method of treating functional dyspepsia in a patient in need thereof, comprising administering to the patient a therapeutically effective amount of Compound (I) form 1 or Compound (I) form 3.

Skeletal Muscle Contusion

Skeletal muscle contusion indicates a direct, blunt, compressive force to a muscle. Contusions are one of the most common sports-related injuries. The severity of contusions ranges from simple skin contusions to muscle and bone contusions to internal organ contusions. In third party data, MAGL inhibition demonstrated anti-inflammatory effects in a rat skeletal muscle contusion model.

In some embodiments, MAGL inhibitors described herein have efficacy in treatment of skeletal muscle contusion. In some embodiments, disclosed herein is a method of treating a skeletal muscle contusion in a patient in need thereof, comprising administering to the patient a therapeutically effective amount of Compound (I) form 1 or Compound (I) form 3.

Multiple Sclerosis Symptomatic Treatment

Nearly all MS patients of all subtypes have one or more symptoms of spasticity, pain, disturbed sleep, bladder dysfunction, and fatigue. Disease modifying therapies do not improve symptoms. Spasticity affects over 80% of MS patients; 34% have moderate, severe, or total spasticity. Severe spasticity is related to cost and level of care, and is independently related to quality of life in MS. Two recent reviews support the use of exocannabinoids for the treatment of MS spasticity and pain (Whiting et al., JAMA. 2015); Hill et al., JAMA. 2015).

An exocannabinoid preparation is an approved treatment for spasticity associated with MS. Sativex, an oromucosal spray mixture of the $CB_1$ agonist THC and another cannabis plant derived alcohol, cannabidiol, was shown to decrease self-reported spasticity related symptoms. In a pivotal trial of Sativex using a randomized withdrawal design, there was improvement with continuing Sativex in spasm frequency, sleep disruption by spasticity, subject global impression of change, carer global impression of change, and physician global impression of change. Other clinical trials have shown activity of a variety of exocannabinoids in spasticity due to MS (Zajicek et al., Lancet. 2003; Collin et al., Eur J Neurol. 2007; Collin et al., Neurol Res. 2010). These parallel group studies exemplify the clinical trial design and endpoints that could be used to show a MAGL benefits spasticity in MS.

In an embodiment, disclosed herein is a crystalline form of Compound (I) for use in the treatment of multiple sclerosis.

In an embodiment, disclosed herein is a crystalline form of Compound (I) for use in the treatment of one or more symptoms in multiple sclerosis selected from fatigue, spasticity, depression, behavioral disturbance, irritability-agitation, and pain.

In a further embodiment, disclosed herein is a crystalline form of Compound (I) for use in the treatment of spasticity.

It is believed that a MAGL will also be beneficial in the treatment of indications related to autoimmune encephalomyelitis. Hence, in a further embodiment, disclosed herein is a crystalline form of Compound (I) for use in the treatment of Rasmussen encephalitis, Systemic lupus erythematosus, Behcet's disease, Hashimoto's encephalopathy, and Sydenham's chorea.

Combination Therapies

Also contemplated herein are combination therapies, for example, co-administering crystalline forms of Compound (I) and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is affected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain, a crystalline form of Compound (I) is co-administered with another therapeutic for pain such as an opioid, a cannabinoid receptor ($CB_1$ or $CB_2$) modulator, a COX-2 inhibitor, acetaminophen, and/or a non-steroidal anti-inflammatory agent. Additional therapeutics e.g., for the treatment of pain that are co-administered, include morphine, pregabalin, gabapentin, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

EXPERIMENTAL SECTION

List of Abbreviations

As used above, and throughout the description of the invention, the following abbreviations, unless otherwise indicated, shall be understood to have the following meanings:

| | |
|---|---|
| t-Bu: | tert-butyl |
| DCM: | dichloromethane ($CH_2Cl_2$) |
| DMF: | dimethylformamide |
| DMSO: | dimethylsulfoxide |
| equiv: | equivalent(s) |
| EtOH: | ethanol |
| EtOAc: | ethyl acetate |
| HPLC: | high performance liquid chromatography |
| i-PrOAc: | isopropyl acetate |
| MS: | mass spectroscopy |
| NMR: | nuclear magnetic resonance |
| MeCN: | acetonitrile |
| 2-MeTHF: | 2-Methyltetrahydrofuran |
| MIBK: | Methyl isobutyl ketone |
| MTBE: | Methyl Tert-Butyl Ether |
| TFA: | trifluoroacetic acid |
| TGA: | Thermo-gravimetric Analysis |
| RT: | room temperature |
| XRPD | X-ray powder diffraction |
| DSC, | Differential Scanning Calorimetry |
| DVS | Dynamic vapor sorption |
| LC-MS | Liquid chromatography-mass spectrometry |

Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized.

Analytical Methods

LC-MS Methods

The analytical LC-MS system is equipped with Shimadzu LCMS-2020, PDA detector (operating at 254 nm), ELSD detector, and ESI-source operating in positive ion mode.

LC-conditions:

Method C: The column is Express C18 50*3.0 mm operating at 40° C. with 1.5 mL/min of a binary gradient consisting of water+0.05% TFA (A) and ACN+0.05% TFA (B). The retention times ($t_R$) are expressed in minutes based on UV-trace at 254 nm.

| Gradient: | 0.01 min | 20% B |
|---|---|---|
| | 3.50 min | 50% B |
| | 4.30 min | 95% B |
| | 4.00 min | 95% B |
| | 5.10 min | 5% B |

Method O: The column is HALO C18 30*3.0 mm, 2 μm operating at 40° C. with 1.5 mL/min of a binary gradient consisting of water+0.05% TFA (A) and ACN+0.05% TFA (B). The retention times ($t_R$) are expressed in minutes based on UV-trace at 200 nm.

| Gradient: | 2.20 min | 100% B |
|---|---|---|
| | 2.70 min | 100% B |
| | 2.72 min | 5% B |
| Total run time: | 3.0 min | |

$^1$H NMR Method $^1$H NMR spectra were recorded at 300 or 400 MHz on a Bruker Avance HD. Chemical shift values are expressed in ppm-values relative to tetramethylsilane. The following abbreviations or their combinations are used for multiplicity of NMR signals: br=broad, d=doublet, dd=doublet of doublets, dt=doublet of triplets, hept=heptet, m=multiplet, q=quartet, quint=quintet, s=singlet, t=triplet, td=triplet of doublets.

Example 1: Synthesis of Compound (I) Form 1

Step 1: Synthesis of 1-benzyl 6-(t-butyl) 6-azaspiro[2.5]octane-1,6-dicarboxylate

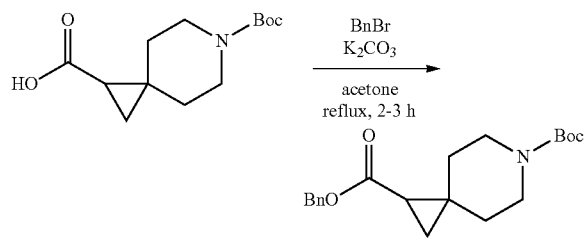

Into a flask purged and maintained with an inert atmosphere of nitrogen, was added a solution of 6-(t-butoxycarbonyl)-6-azaspiro[2.5]octane-1-carboxylic acid (240 g) in acetone (5 L). Benzyl bromide (170.6 g) and $K_2CO_3$ (259.8 g) were added. The resulting solution was refluxed for 2-3 h. The reaction was then cooled to room temperature and filtered. The filter cake was washed with ethyl acetate. The combined filtrate was concentrated under vacuum, resulting in 297 g of crude 1-benzyl 6-(t-butyl) 6-azaspiro[2.5]octane-1,6-dicarboxylate.

Step 2: Synthesis of benzyl 6-azaspiro[2.5]octane-1-carboxylate hydrochloride

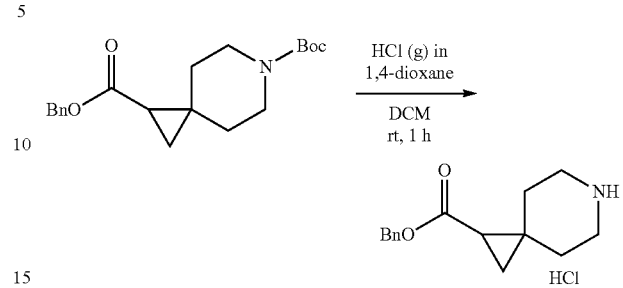

Into a flask purged and maintained with an inert atmosphere of nitrogen, was added a solution of crude 1-benzyl 6-(t-butyl) 6-azaspiro[2.5]octane-1,6-dicarboxylate (297 g) in DCM (1.5 L). HCl (g) in 1,4-dioxane (4M, 1.5 L) was added dropwise. The resulting solution was stirred for 1 h at room temperature and concentrated under vacuum. The crude product was slurried with $Et_2O$ (10 V) to provide 198.3 g of benzyl 6-azaspiro[2.5]octane-1-carboxylate.

Step 3: Synthesis of 1-benzyl 6-(1,1,1,3,3,3-hexafluoropropan-2-yl) 6-azaspiro[2.5]octane-1,6-dicarboxylate

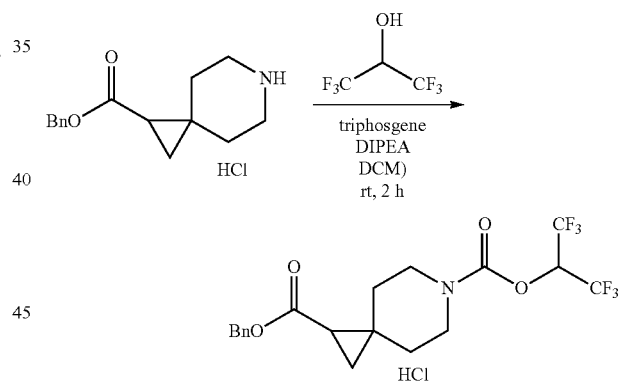

Into a flask purged and maintained with an inert atmosphere of nitrogen, was added a solution of 1,1,1,3,3,3-hexafluoropropan-2-ol (393 g) in DCM (2 L). The mixture was cooled to 0° C. and triphosgene (106.9 g) was added in batches. DIPEA (550 g) was then added dropwise at 0-10° C. The mixture was stirred for 1.5 h at this temperature. A solution of benzyl 6-azaspiro[2.5]octane-1-carboxylate hydrochloride (198 g) in DCM (2 L) was then added dropwise at 0° C. The resulting solution was stirred at room temperature for 2 h. The reaction mixture was quenched by pouring into water (6 L), then extracted with DCM (2×2 L). The combined organic layers were washed with brine (1×3 L), dried over anhydrous sodium sulfate and concentrated under vacuum. The residue was chromatographed on a silica gel column with EtOAc/petroleum ether (1/30), resulting in 265 g of 1-benzyl 6-(1,1,1,3,3,3-hexafluoropropan-2-yl) 6-azaspiro[2.5]octane-1,6-dicarboxylate.

Step 4: Isolation of (S)-1-benzyl 6-(1,1,1,3,3,3-hexafluoropropan-2-yl) 6-azaspiro[2.5]octane-1,6-dicarboxylate (Intermediate 2A) and (R)-1-benzyl 6-(1,1,1,3,3,3-hexafluoropropan-2-yl) 6-azaspiro[2.5]octane-1,6-dicarboxylate (Intermediate 3A)

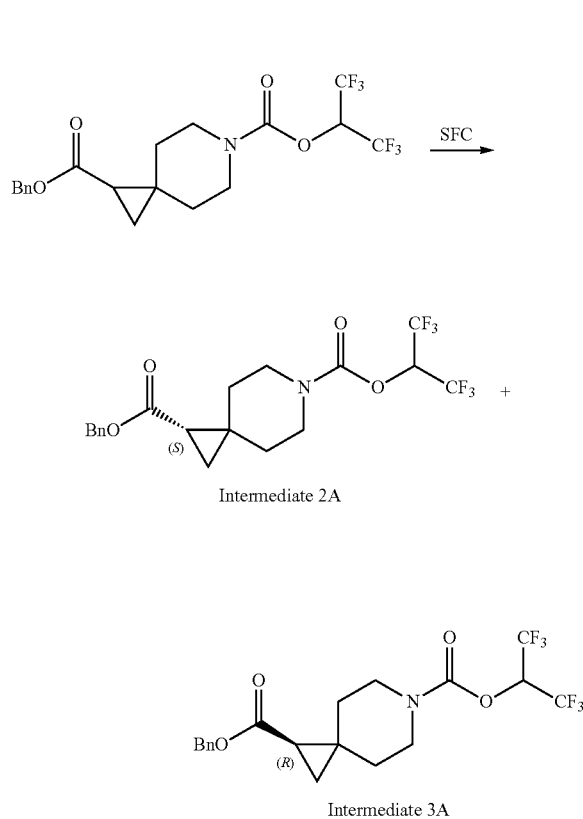

Intermediate 2A

Intermediate 3A

The racemic mixture of 1-benzyl 6-(1,1,1,3,3,3-hexafluoropropan-2-yl) 6-azaspiro[2.5]octane-1,6-dicarboxylate (265 g) prepared in Step 3 was separated by preparative SFC-HPLC (Column: CHIRALPAK IG-3 3.0*50 mm, 3 μm; Mobile Phase: Phase A: $CO_2$, phase B: MeOH (0.1% DEA); Flow rate: 2 mL/min; Gradient: 2% B; 220 nm) to afford Intermediate 2A and 2B. The absolute configuration was confirmed by a Vibrational Circular Dichroism (Appl. Spectrosc. 65 (7), 699 (2011); PCT/EP2021/081522) study. The spectrum was obtained with a ChiralIR with DualPEM VCD-spectrometer and was compared with calculated values (methodology and basis set for DFT calculations=B3LYP/6311Gdp with CPCM (chloroform)).

Intermediate 2A; 110 g of (S)-1-benzyl 6-(1,1,1,3,3,3-hexafluoropropan-2-yl) 6-azaspiro[2.5]octane-1,6-dicarboxylate. $^1$H NMR (300 MHz, Chloroform-d) δ 7.46-7.28 (m, 5H), 5.75 (p, J=6.3 Hz, 1H), 5.13 (s, 2H), 3.57 (m, 3H), 3.28 (m, 1H), 1.86-1.61 (m, 3H), 1.56-1.36 (m, 2H), 1.27-1.19 (m, 1H), 0.99 (dd, J=8.2, 4.7 Hz, 1H). $t_R$=1.572 min. LCMS (Method O) (ESI, m/z): 440 [M+H]$^+$ and Intermediate 3A; 100 g of 1-benzyl 6-(1,1,1,3,3,3-hexafluoropropan-2-yl) (R)-6-azaspiro[2.5]octane-1,6-dicarboxylate. $^1$H NMR (300 MHz, Chloroform-d) δ 7.36 (d, J=2.6 Hz, 5H), 5.75 (p, J=6.3 Hz, 1H), 5.13 (d, J=1.4 Hz, 2H), 3.71-3.40 (m, 3H), 3.39-3.13 (m, 1H), 1.71 (ddd, J=29.4, 9.4, 5.2 Hz, 3H), 1.57-1.36 (m, 2H), 1.23 (d, J=5.2 Hz, 1H), 0.99 (dd, J=8.1, 4.7 Hz, 1H). $t_R$=1.572 min. LCMS (Method O) (ESI, m/z): 440 [M+H]$^+$.

Step 5: Synthesis of (S)-6-(((1,1,1,3,3,3-hexafluoropropan-2-yl)oxy)carbonyl)-6-azaspiro[2.5]octane-1-carboxylic acid (Intermediate 2B)

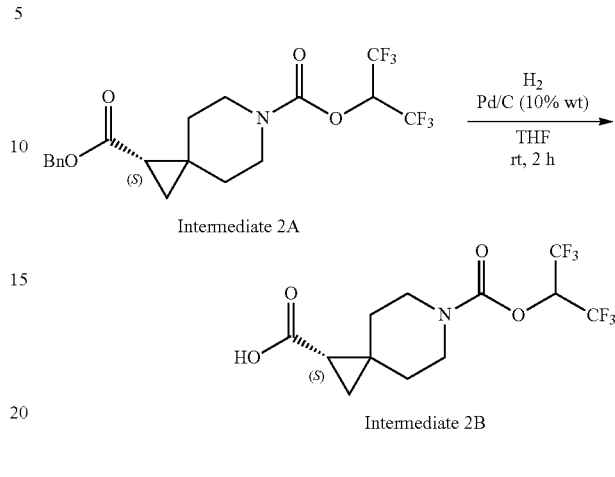

Intermediate 2A

Intermediate 2B

A solution of 1-benzyl 6-(1,1,1,3,3,3-hexafluoropropan-2-yl) (S)-6-azaspiro[2.5]octane-1,6-dicarboxylate (110 g) in THF (2 L) was added to a flask. Wet Pd/C (22 g, 10% wt, 50% $H_2O$) was added to the mixture. The resulting mixture was purged and replaced with $H_2$ three times and then stirred under $H_2$ for 3 h at room temperature. The mixture was filtered, and the filter cake was washed with THF (2×500 mL). The combined filtrate was concentrated under vacuum, and the crude product was co-evaporated with toluene (2×1 L), resulting in 90 g of crude (S)-6-(((1,1,1,3,3,3-hexafluoropropan-2-yl)oxy)carbonyl)-6-azaspiro[2.5]octane-1-carboxylic acid (Intermediate 2B). 0.2 g of crude product was purified by silica column chromatography to provide pure characterization data. $^1$H NMR (300 MHz, Chloroform-d) δ 5.78 (h, J=6.3 Hz, 1H), 3.79-3.40 (m, 4H), 1.85 (q, J=6.1 Hz, 2H), 1.65 (dd, J=8.0, 5.4 Hz, 1H), 1.54 (dq, J=10.9, 5.8, 5.0 Hz, 2H), 1.28 (t, J=5.1 Hz, 1H), 1.09 (dd, J=8.1, 4.8 Hz, 1H). $t_R$=1.441 min. LCMS (Method O) (ESI, m/z): 350 [M+H]$^+$.

Step 6: Synthesis of Compound (I) Form 1

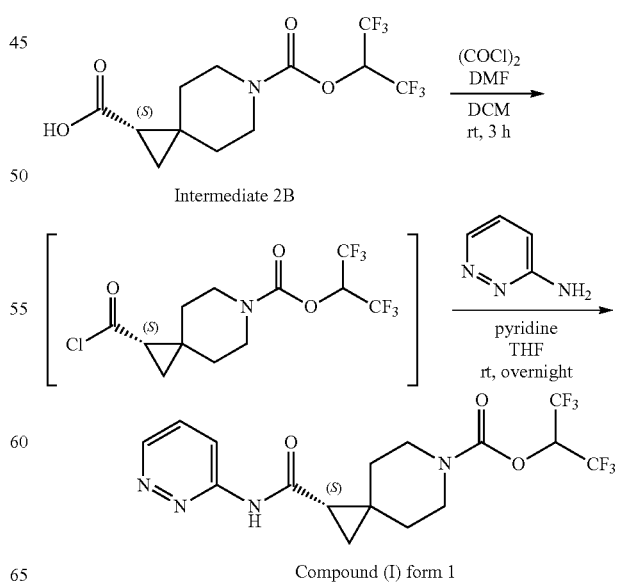

Intermediate 2B

Compound (I) form 1

Into a flask purged and maintained with an inert atmosphere of nitrogen, was added (S)-6-(((1,1,1,3,3,3-hexafluoropropan-2-yl)oxy)carbonyl)-6-azaspiro[2.5]octane-1-carboxylic acid (Intermediate 2B) (38.5 g), DCM (800 mL) and DMF (0.40 g). The mixture was cooled to 0° C. and (COCl)$_2$ (11.5 g) was added dropwise. The resulting mixture was stirred at room temperature for 3 h. The mixture was then concentrated under vacuum to obtain crude acyl chloride for later use. Into another flask purged and maintained with an inert atmosphere of nitrogen, was added pyridazin-3-amine (12.6 g), pyridine (17.4 g) and THF (800 mL). The solution of previous acyl chloride in THF (500 mL) was added dropwise at room temperature. The resulting solution was stirred overnight at room temperature. After complete reaction, the mixture was diluted with 3 L of ice water and extracted with EtOAc (2×1 L). The combined organic phases were washed with H$_2$O (1×1 L) and brine (1×1 L), dried over anhydrous Na$_2$SO$_4$ and concentrated under vacuum. The residue was purified by silica gel column chromatography with EtOAc/petroleum ether (1/10), to provide 34.3 g of product. The product was slurried with n-hexane (20 V) and filtered to obtain 26.7 g of 1,1,1,3,3,3-hexafluoropropan-2-yl (S)-1-(pyridazin-3-ylcarbamoyl)-6-azaspiro[2.5]octane-6-carboxylate. The product was isolated by slurry with n-heptane (10 V) to provide 24.13 g of Compound (I) form 1. $^1$H NMR (300 MHz, Chloroform-d) δ 10.82 (s, 1H), 8.87 (d, J=4.7 Hz, 1H), 8.61 (d, J=9.1 Hz, 1H), 7.55 (s, 1H), 5.90-5.62 (m, 1H), 3.73-3.27 (m, 4H), 2.26 (dd, J=8.0, 5.4 Hz, 1H), 1.95-1.72 (m, 4H), 1.41 (t, J=5.0 Hz, 1H), 1.11 (dd, J=7.9, 4.6 Hz, 1H). t$_R$=1.443 min. LCMS (Method O) (ESI, m/z): 427 [M+H]$^+$. CHIRALPAK AD, 3.0*100 mm, 3 mm; mobile phase: Phase A: CO$_2$, phase B: MeOH (0.1% DEA); flow rate: 2 mL/min; gradient: 10% to 50% in 2.0 min, hold 1.0 min at 50%; detection: 220 nm: t$_R$=1.032 min.

Example 2: Preparation of Compound (I) Form 3

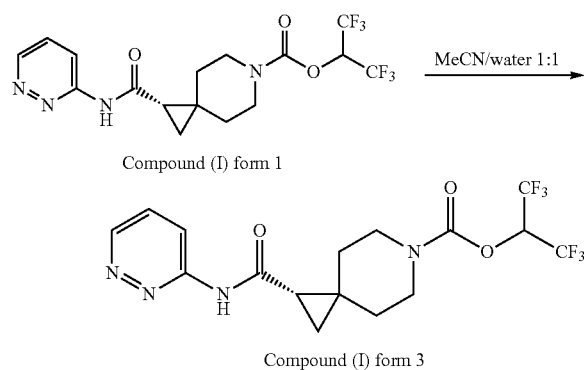

In a vial Compound (I) form 1 (500 mg) were slurried in a 1:1 mixture of MeCN/water at room temperature for 24 hours. A small sample of wet precipitate was analyzed by XRPD showing the diffractogram of FIG. 3.

Example 3: XRPD Measurements

X-Ray powder diffractograms were measured on a PANalytical X'Pert PRO X-Ray Diffractometer using CuKa1 radiation (λ=1.5406 Å). The samples were measured in reflection mode in the 2θ range 3-40° using an PIXcel detector.

TABLE 1

Charateristic XRPD peaks of the crystalline forms of Compound (I)

| Crystalline form | Peaks expressed in degree of diffraction angle [°2θ] |
|---|---|
| Compound (I) form 1 | 10.81, 16.54, 16.76, and 19.21 |
| Compound (I) form 3 | 6.61, 9.16, 13.09, and 14.32 |

XRPD Analysis of the Obtained Compounds

XRPD analysis (FIG. 1) of Compound (I) form 1 showed the form to be crystalline.

XRPD analysis (FIG. 3) of Compound (I) form 3 showed the form to be crystalline.

Example 4: Thermo-Gravimetric Analysis (TGA)

TGA was measured using a TA-instruments Discovery TGA. 1-15 mg sample is heated 10° C./min in an open pan under nitrogen flow.

TGA analysis (FIG. 2) of Compound (I) form 1 showed the form to be unsolvated/unhydrated.

TGA analysis (FIG. 4) of Compound (I) form 3 showed the form to be unsolvated/unhydrated.

Example 5: Differential Scanning Calorimetry (DSC)

DSC was measured using a TA-Instruments Discovery-DSC calibrated at 5°/min to give the melting point as onset value. About 2 mg of sample is heated 5°/min under nitrogen flow in a closed pan with a pinhole in the lid.

Figure 5:
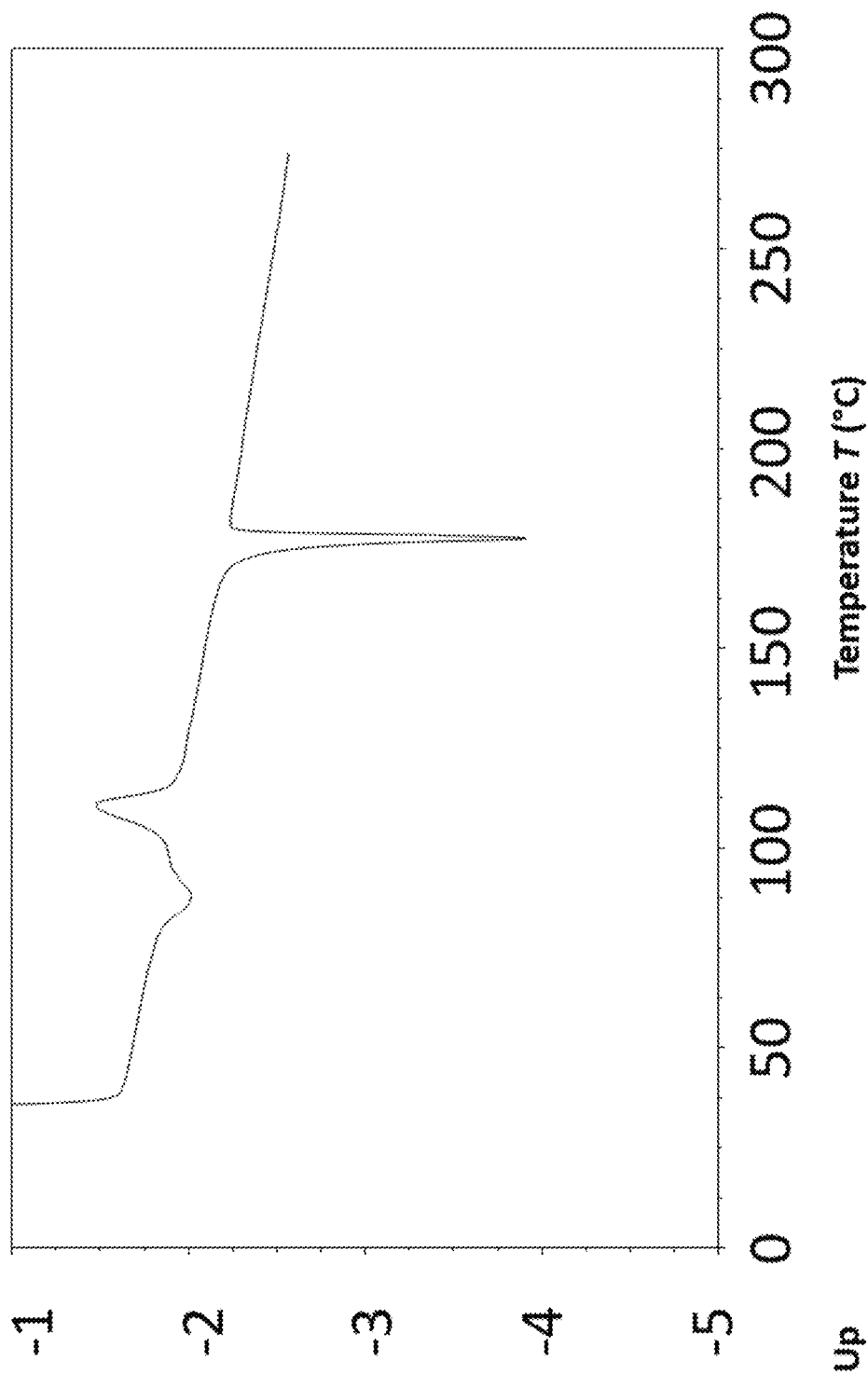
FIG. 5 shows a differential scanning calorimetry (DSC) thermogram of Compound (I) form 1. X-axis: Temperature (° C.); Y-axis: normalized heat flow (W/g).
Figure 6:
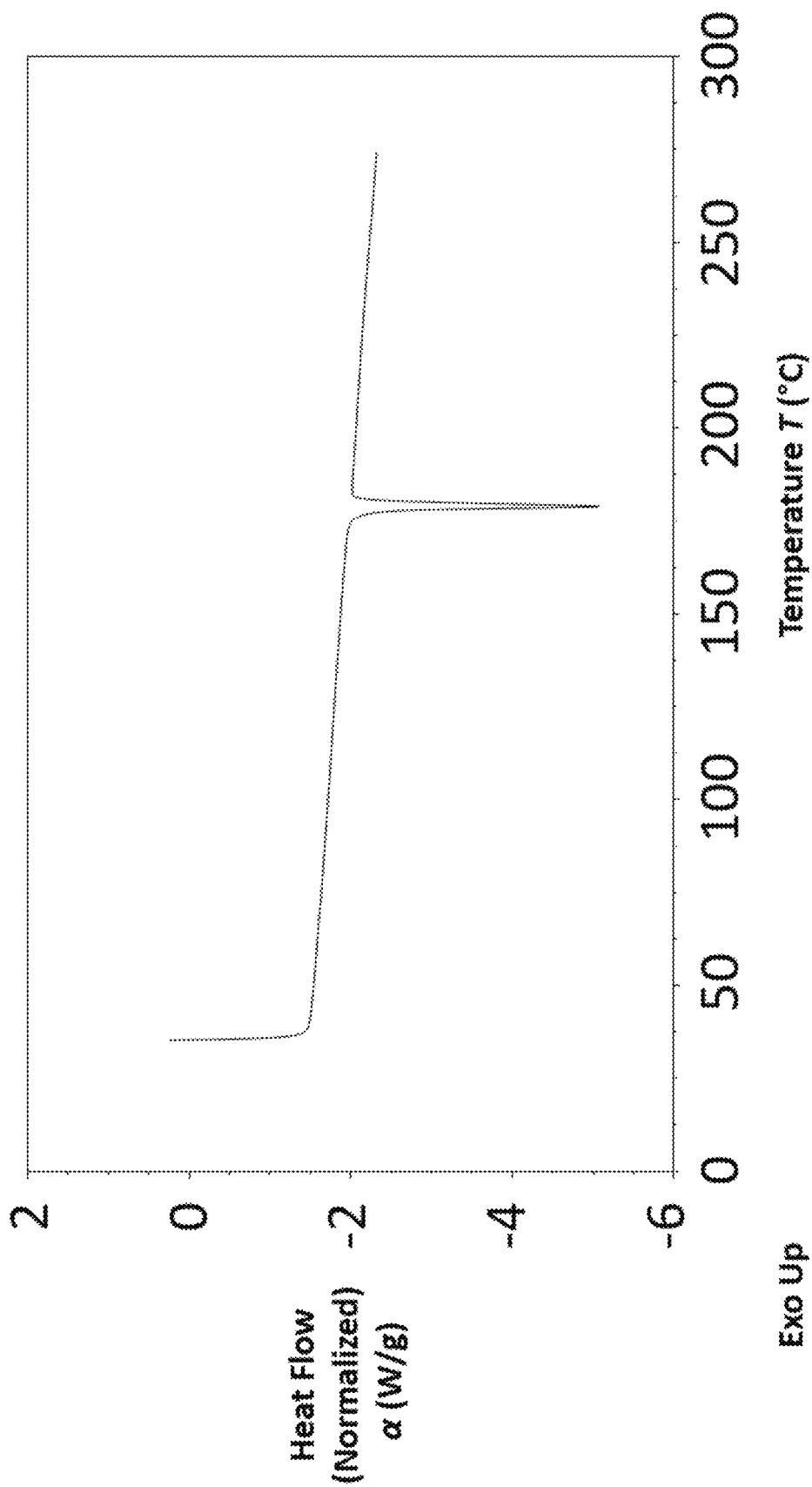
FIG. 6 shows a differential scanning calorimetry (DSC) thermogram of Compound (I) form 3. X-axis: Temperature (° C.); Y-axis: normalized heat flow (W/g).
Figure 7:
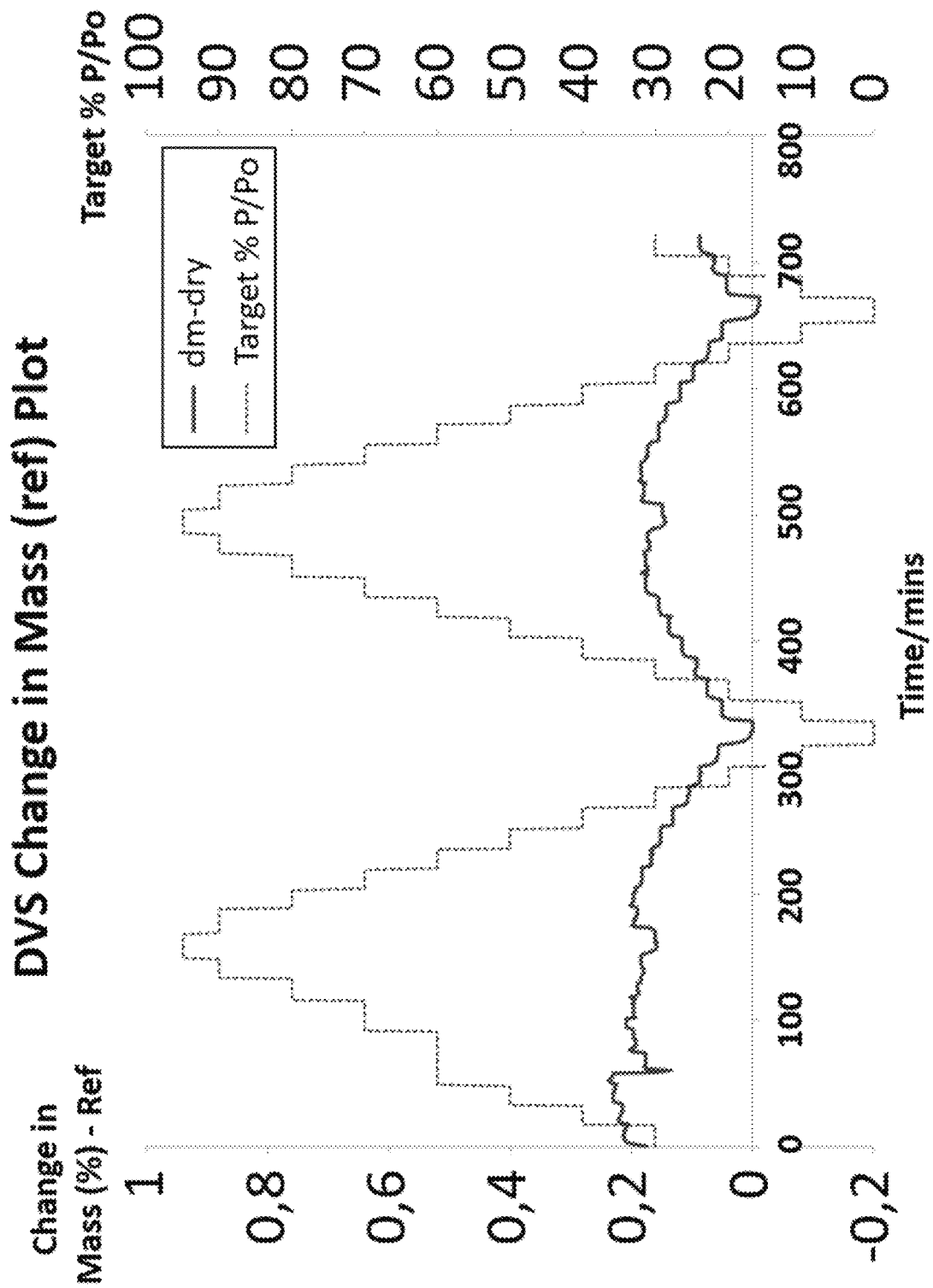
FIG. 7 shows a dynamic vapor sorption (DVS) sorption kinetic plot of Compound (I) form 1. X-axis: Time (min); Y-axis (left): Change in mass (%); Y-axis (right): Relative humidity (%).
Figure 8:
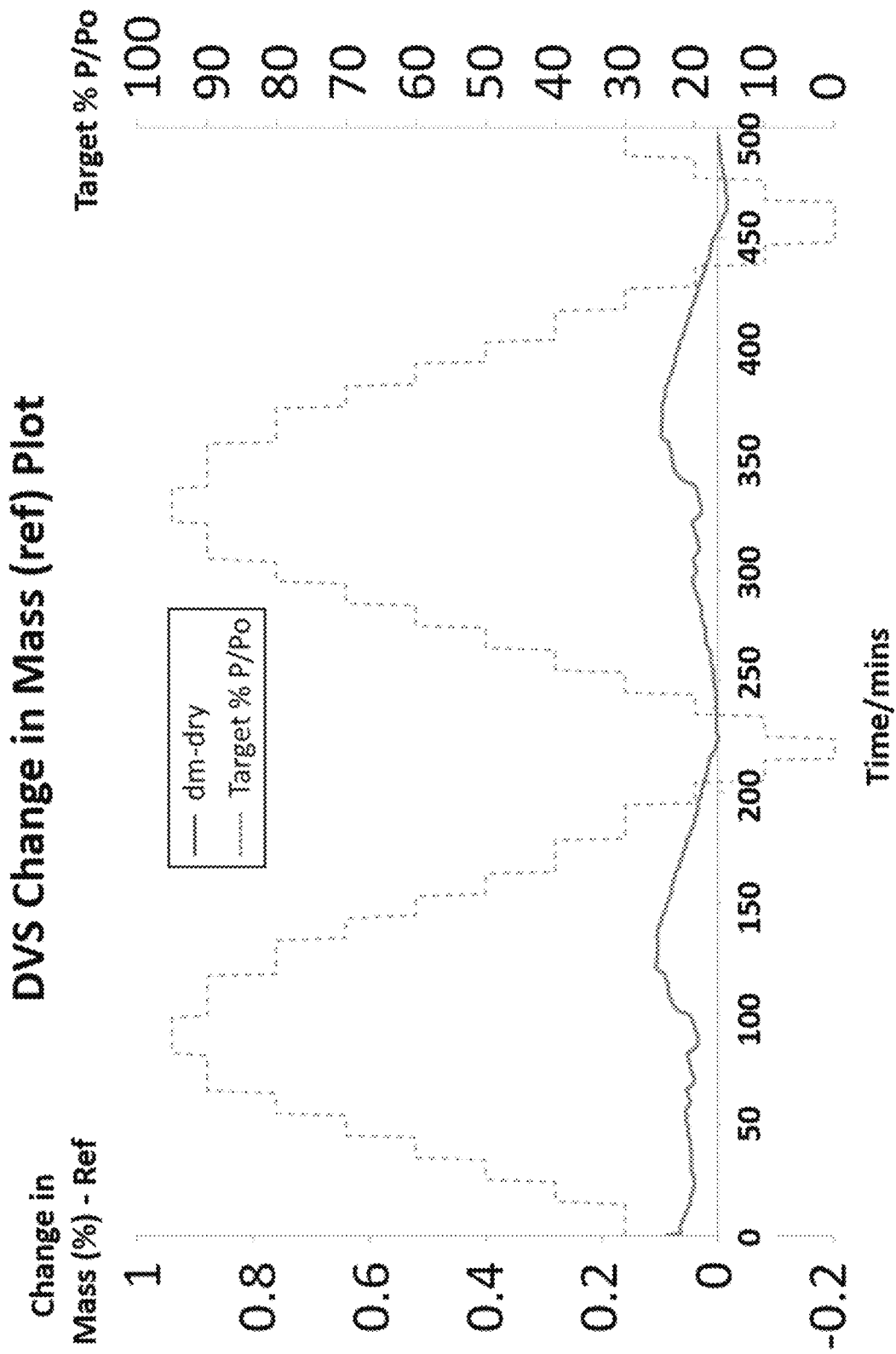
FIG. 8 shows a dynamic vapor sorption (DVS) sorption kinetic plot of Compound (I) form 3. X-axis: Time (min); Y-axis (left): Change in mass (%); Y-axis (right): Relative humidity (%).

The curve on FIG. 5 shows an exotherm between two endothermy. XRPD after heating a sample of Compound (I) form 1 to 150° C. showed Compound (I) Form 3. Thus, Compound (I) Form 3 was formed upon heating of Compound (I) Form 1. This formation of Compound (I) Form 3 at high temperature combined with the change from Compound (I) Form 1 into Compound (I) Form 3 upon slurry indicates that compound (I) Form 3 is thermodynamically more stable than Compound (I) Form 1.

Example 6: Procedures Used for Dynamic Vapor Sorption (DVS) Measurements

DVS was measured using SMS DVS advantage 01 changing the relative humidity from 0% RH to 95% RH in steps of 10% RH (5% between 90 and 95% RH). 2 cycles were performed using 1-10 mg, starting at 30% RH.

DVS analysis of Compound (I) form 1 showed the form to be slightly hygroscopic with water uptake of 1.4 wt % up to 90% RH.

DVS analysis of Compound (I) form 3 showed the form to be less hygroscopic than form 1 with a water uptake of around 0.1 wt % up to 90% RH.

Example 7—Biological Evaluation

Compound (I) was tested to assess their MAGL activity using the following in vitro and in vivo assays.
In Vitro Competitive Activity-Based Protein Profiling
PC3 human cell membrane proteomes (50 μL, 2.0 mg/mL total protein concentration) were preincubated with varying concentrations of Compound (I) at 37° C. After 30 min, the ABPP probe JW912-Bodipy (1.0 μL, 50 μM in DMSO) was added and the mixture was incubated for 30 min at room temperature. Reactions were quenched with SDS loading buffer (15 μL—4×) and run on SDS-PAGE. Following gel imaging, serine hydrolase activity was determined by measuring fluorescent intensity of gel bands corresponding to MAGL using ImageJ 1.43u software. Intensities were converted to percent enzyme activity by normalizing to DMSO controls. IC50 values were determined by fitting percent enzyme activities to a non-linear regression, 4-parameter, sigmoidal dose response function in Prism GraphPad.

In Vitro Competitive Substrate Hydrolysis Enzyme Activity Assay

HEK293 cell lysates expressing recombinant human MAGL enzyme and 4-nitrophenyl acetate (pNPA) substrate were diluted separately in 50 mM HEPES (pH 7.0) containing 200 mM KCl and 1 mM EDTA. Lysates (50 μL, ~1.2 μg total protein) were preincubated with varying concentrations of Compound (I) at 25° C. After 30 min, 2×pNPA substrate (50 μL, 2.5 mM) was added and the rate of substrate turnover was monitored by measuring the increase in absorbance at wavelength 405 nm for 20 minutes at 25° C. using a Biotek Neo2 plate reader. The mean velocity was converted to percent enzyme activity following background subtraction and normalization to DMSO controls. IC50 values were determined by fitting percent enzyme activities to a non-linear regression, 4-parameter, sigmoidal dose response function in Prism GraphPad.

In Vivo

Compound (I) were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 2.

TABLE 2

MAGL activity in-vivo and in vitro of Compound (I)

| Ex | MAGL % inh. 1 μM (human PC3) | MAGL IC$_{50}$ (μM) (human HEK293) | MAGL IC$_{50}$ (μM) (human PC3) | MAGL % inh. 5 mg/kg (mouse) |
|---|---|---|---|---|
| Compound (I) | 100 | 0.00826 | 0.0046 | 100 |

We claim:

1. A crystalline form of 1,1,1,3,3,3-Hexafluoropropan-2-yl(S)-1-(pyridazin-3-ylcarbamoyl)-6-azaspiro[2.5]octane-6-carboxylate form 3, characterized by having an X-ray powder diffraction obtained using CuKα1 radiation (λ=1.5406 Å) comprising peaks at the following 2θ-angles: 6.61°, 9.16°, 13.09°, and 14.32°.

2. A solid dosage form comprising the crystalline form of claim 1, and one or more pharmaceutically acceptable carriers or diluents.

3. The solid dosage form of claim 2, wherein the solid dosage form is selected from capsules, tablets, dragées, pills, lozenges, powders or granules.

4. The solid dosage form of claim 2, wherein the solid dosage form is a tablet.

5. The solid dosage form of claim 2, wherein the dosage form contains the crystalline form of 1,1,1,3,3,3-Hexafluoropropan-2-yl(S)-1-(pyridazin-3-ylcarbamoyl)-6-azaspiro[2.5]octane-6-carboxylate form 3 in an amount from 0.1 to 200 mg.

6. The solid dosage form of claim 2, wherein the dosage form contains the crystalline form of 1,1,1,3,3,3-Hexafluoropropan-2-yl(S)-1-(pyridazin-3-ylcarbamoyl)-6-azaspiro[2.5]octane-6-carboxylate form 3 in an amount from 1 to 40 mg.

7. The solid dosage form of claim 2, wherein the dosage form contains the crystalline form of 1,1,1,3,3,3-Hexafluoropropan-2-yl(S)-1-(pyridazin-3-ylcarbamoyl)-6-azaspiro[2.5]octane-6-carboxylate form 3 in an amount from 1 to 30 mg.

8. The solid dosage form of claim 2, wherein the dosage form contains the crystalline form of 1,1,1,3,3,3-Hexafluoropropan-2-yl(S)-1-(pyridazin-3-ylcarbamoyl)-6-azaspiro[2.5]octane-6-carboxylate form 3 in an amount from 1 to 20 mg.

9. A method for treating atopic dermatitis, bladder dysfunction associated with multiple sclerosis, contact dermatitis, dermatomyositis, eczema, enteritis, fibromyalgia, inflammatory bowel disease, interstitial cystitis, irritable bowel syndrome, ischemia, abdominal pain, abdominal pain associated with irritable bowel syndrome, acute pain, back pain, cancer pain, chest pain, functional chest pain, joint pain, menstrual pain, musculoskeletal diseases, peripheral neuropathy, migraine, visceral hypersensitivity osteoarthritis, pharyngitis, post mastectomy pain syndrome, post trigeminal neuralgia, post-operative pain, post-traumatic stress disorder, skeletal muscle contusion, skin diseases, sunburn, systemic lupus erythematosus, toothache, vasoocclusive painful crises in sickle cell disease, or visceral pain in a patient in need thereof; wherein the method comprises administering to the patient a therapeutically effective amount of the crystalline form of 1,1,1,3,3,3-Hexafluoropropan-2-yl(S)-1-(pyridazin-3-ylcarbamoyl)-6-azaspiro[2.5]octane-6-carboxylate form 3 of claim 3.

* * * * *